United States Patent
Sema

(10) Patent No.: US 9,616,003 B2
(45) Date of Patent: Apr. 11, 2017

(54) ANTIBACTERIAL MOUTHWASH WHICH IS NONTOXIC IN CELLULAR LEVEL

(71) Applicant: Hakki Sema, Konya (TR)

(72) Inventor: Hakki Sema, Konya (TR)

( * ) Notice: Subject to any disclaimer, the term of this patent is extended or adjusted under 35 U.S.C. 154(b) by 0 days.

(21) Appl. No.: 14/422,705

(22) PCT Filed: May 31, 2013

(86) PCT No.: PCT/TR2013/000176
§ 371 (c)(1),
(2) Date: Feb. 20, 2015

(87) PCT Pub. No.: WO2013/180679
PCT Pub. Date: Dec. 5, 2013

(65) Prior Publication Data
US 2015/0209247 A1     Jul. 30, 2015

(30) Foreign Application Priority Data
May 31, 2012 (TR) ................ a 2012 06408

(51) Int. Cl.
| | | |
|---|---|---|
| *A61K 8/19* | (2006.01) | |
| *A61Q 11/00* | (2006.01) | |
| *A61Q 17/00* | (2006.01) | |
| *A61K 9/00* | (2006.01) | |

(52) U.S. Cl.
CPC .............. *A61K 8/19* (2013.01); *A61K 9/0063* (2013.01); *A61Q 11/00* (2013.01); *A61Q 17/005* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 3,542,917 A | | 11/1970 | Schwartz et al. |
| 4,132,770 A | * | 1/1979 | Barth ................ 424/49 |
| 4,145,242 A | * | 3/1979 | Chow ............ B27D 1/00 |
| | | | 106/286.8 |
| 4,610,790 A | * | 9/1986 | Reti ............. A61L 2/022 |
| | | | 210/259 |
| 5,028,414 A | | 7/1991 | Sampathkumar |
| 2004/0067203 A1 | * | 4/2004 | Parikh ............. A61K 8/33 |
| | | | 424/49 |

FOREIGN PATENT DOCUMENTS

| | | | | |
|---|---|---|---|---|
| CN | 101708149 A | | 5/2010 | |
| GB | 689679 | * | 4/1953 | ............ 4/348 |
| GB | 689679 A | | 4/1953 | |
| GB | 1311060 A | | 3/1973 | |
| RU | 2197950 C2 | | 2/2003 | |

* cited by examiner

*Primary Examiner* — Frederick Krass
*Assistant Examiner* — Celeste A Roney
(74) *Attorney, Agent, or Firm* — Gokalp Bayramoglu

(57) ABSTRACT

The invention is antibacterial mouthwash which does not have any side effects as it does not have toxicity in cellular level during the fight against oral cavity diseases and which is used for eliminating microbial dental plaques.

1 Claim, No Drawings

ANTIBACTERIAL MOUTHWASH WHICH IS NONTOXIC IN CELLULAR LEVEL

FIELD OF THE INVENTION

The invention is related to antibacterial mouthwash used for eliminating microbial dental plaques especially in the treatment of periodontal diseases.

PRIOR ART

Periodontal diseases are a group of inflammatory diseases that affect and destruct the supporting tissues of teeth, ie. gingiva, alveolar bone, periodontal ligament, cementum. One or more teeth may be involved in periodontal diseases and when left untreated, they may cause to tooth loss.

When the teeth were not brushed effectively, tight and colorless accumulation including microorganisms, leukocytes, dead epithelial cells, salivary proteins and food remnants, called microbial dental plaque develops on tooth surface. The plaque adheres onto the teeth surfaces especially along the rough surfaces and it settles down between the gingiva, in the cracks of enamel and on the surface of tartar. This plaque biofilm initiates inflammation in the gingiva. Periodontal diseases are chronic bacterial infections affecting the gingiva and the alveolar bones of the teeth. They are separated into two main groups as gingivitis and periodontitis. Gingivitis is the mild form of the disease which is limited to the gingiva and its symptoms are redness, swelling and easy bleeding of the gingiva. Gingivitis is generally caused by improper oral hygiene and it is recoverable with a first line treatment including tartar removal, polishing and oral hygiene motivation, as well as with a proper oral care. Gingivitis may turn into periodontitis if it is not treated. In course of time, the plaque advances beneath the gingiva, the bacterial toxins irritate the gingiva and initiate chronic inflammation and suddenly, the alveolar bones degrade. Consequently, the gingiva is separated from the tooth and spaces called pockets are formed between the tooth and the gingiva. As the disease progresses, the pockets deepen and more gingiva and bone degrade. In more advanced stages of the disease, the teeth start to swing and it becomes compulsory to pull them.

In the treatment of the periodontal diseases, the elimination of the microbial dental plaque is very important. In the control of dental plaques, the efficiency of the treatment is increased using antibacterial mouthwashes, as well as mechanical periodontal treatment. Most commonly used mouthwashes (as a supplement—with their antibacterial features—for the periodontal treatment) are chlorhexidine mouthwashes. The mouthwash form of chlorhexidine, which is defined as the golden standard among anti-plaque agents, has a broad usage area in dentistry. Chlorhexidine is a mouthwash which has a bisbiguanide structure comprising a digluconate hexamethylene bridge. Chlorhexidine is an effective antimicrobial agent and it has been used as a topical antiseptic for more than 30 years. The efficiency of topical mouthwash form against dental plaque and gingivitis has been shown in several studies. However, chlorhexidine has some side effects. It has been known that chlorhexidine is toxic in cellular level and it may cause dyeing of teeth and other oral surfaces, defects in tasting, burn in the tongue, desquamation in the epithelium cells and allergic reactions. Additionally, it may even cause anaphylactic reaction when it is administered orally. Furthermore, it is a chemotherapeutic which increases the formation of tartar in long term usage.

Although it is very important to use a mouthwash comprising chlorhexidine, overdose or false administration may cause various undesired side effects. It is proven in numerous studies that keeping the mouthwash in oral cavity for a long time causes the development of desquamative lesions in the mandibular mucosa and gingiva. This shows that the wrong usage of mouthwashes containing chlorhexidine causes chemical injuries and allergic reactions.

BRIEF DESCRIPTION OF THE INVENTION

The invention is antibacterial mouthwash which does not have any side effects as it does not have toxicity in cellular level and it is used for eliminating microbial dental plaques in the treatment of periodontal diseases.

DETAILED DESCRIPTION OF THE INVENTION

The invention is antibacterial mouthwash which is used for eliminating microbial dental plaques in the treatment of periodontal diseases and which comprises 0.75% boric acid solution.

12% stock solution is prepared from boric acid (12 g boric acid/100 ml distilled water). $\frac{1}{2}$, $\frac{1}{4}$, $\frac{1}{8}$, $\frac{1}{16}$, $\frac{1}{32}$, $\frac{1}{64}$, $\frac{1}{128}$ dilutions are prepared from this solution. All these processes are carried out in laminar flow cabin II. Solutions are sterilized by filters with a sieve size of 0.22 μm. The pH of the prepared boric acid solution must be 4.9.

The cytotoxicity of the obtained solution is tested by in vitro cell culture (in the gingiva and periodontal ligament cells) studies. It has been found out that, boric acid dilutions diminish the viability of the cells until a dilution of $\frac{1}{16}$. Therefore, when the antibacterial features of the $\frac{1}{16}$ solution—namely 0.75% solution—is tested, it has been found out that the nontoxic dosage of the boric acid maintains its antibacterial features even if it is diluted more.

Antibacterial and anti-inflammatory properties of boric acid are well known. Owing to these properties, the solution obtained from boric acid may be used in periodontal therapy as an adjuvant to the mechanical periodontal therapy. Additionally, as a result of using our invented mouthwash, problems such as dyeing of oral surfaces, defect in tasting, desquamation and allergic reactions experienced with the mouthwashes containing chlorhexidine has been eliminated.

It has been found out that boric acid (0.75%) is better in clinical periodontal parameters compared to normal saline (control) and chlorhexidine groups when it is used as an adjuvant therapy in chronic periodontitis patients in addition to mechanical periodontal therapy. Three-month follow up of enrolled patients has shown no side effects.

According to the obtained results, it is thought that the usage of boric acid solution as an adjuvant to the mechanical periodontal therapy and as an antibacterial mouthwash may be more effective and more advantageous. It is also thought that this solution may be much safer in terms of protecting the oral health in individuals who cannot carry out their own mechanical oral care (the disabled) and who have mouth sores (aphthous lesions, dermatosis).

The invention claimed is:

1. An antibacterial mouthwash, suitable to be safely used as an adjunct to periodontal therapies for humans, consisting of: a 0.75% boric acid solution, which is sterilized using a 0.22 pm filter of $\frac{1}{16}$ dilution that is made from a stock solution prepared with a 12 g pure boric acid and 100 ml distilled water; wherein the pH of the boric acid solution is 4.9 and the antibacterial mouthwash does not reduce cell viability as measured by in vitro cell culture with gingiva and periodontal ligament cells.

* * * * *